_United States Patent_ [19]

Griffith et al.

[11] 4,008,713
[45] Feb. 22, 1977

[54] ULTRASONIC DIAGNOSTIC TECHNIQUE UTILIZING SWITCHED GAIN SIGNAL PROCESSING

[75] Inventors: James M. Griffith; Walter L. Henry, both of Bethesda, Md.

[73] Assignee: The United States of America, Washington, D.C.

[22] Filed: Sept. 18, 1975

[21] Appl. No.: 614,668

[52] U.S. Cl. .......................... 128/2.05 Z; 128/2 V; 73/67.8 R
[51] Int. Cl.² ...................................... A61B 10/00
[58] Field of Search .................. 128/2 V, 2.05 Z; 73/67.7, 67.8 R, 67.8 S, 67.9

[56] References Cited

UNITED STATES PATENTS

| | | | |
|---|---|---|---|
| 3,724,262 | 4/1973 | Niklas | 73/67.8 R |
| 3,789,833 | 2/1974 | Bom | 128/2 V |
| 3,830,223 | 8/1974 | Beretsky | 128/2 V |

*Primary Examiner*—Robert W. Michell
*Assistant Examiner*—Lee S. Cohen
*Attorney, Agent, or Firm*—Holman & Stern

[57] ABSTRACT

An ultrasonic diagnostic technique utilized to determine the wall thickness of cardiac structures. In a preferred embodiment, the endocardial and epicardial surfaces of the left ventricular posterior wall are irradiated with an ultrasonic sound beam. The signal reflected at the epicardial-lung interface is much stronger than the signal from the surrounding myocardium and endocardial surface. In order to simultaneously visualize the endocardial and epicardial reflected signals, the echos received therefrom are processed through a switched gain receiver. That is, an oscillator rapidly switches the receiver gain between two levels that are independently set to display the two wall surfaces, the resultant echocardiogram displaying the high and low gain portions closely mixed whereby the wall thickness may be readily determined.

8 Claims, 3 Drawing Figures

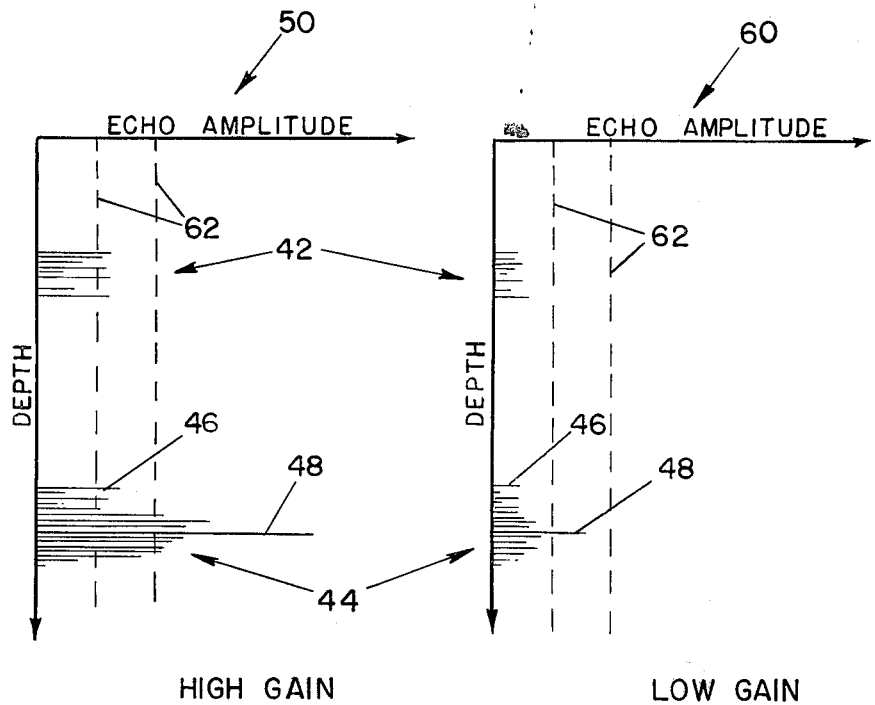
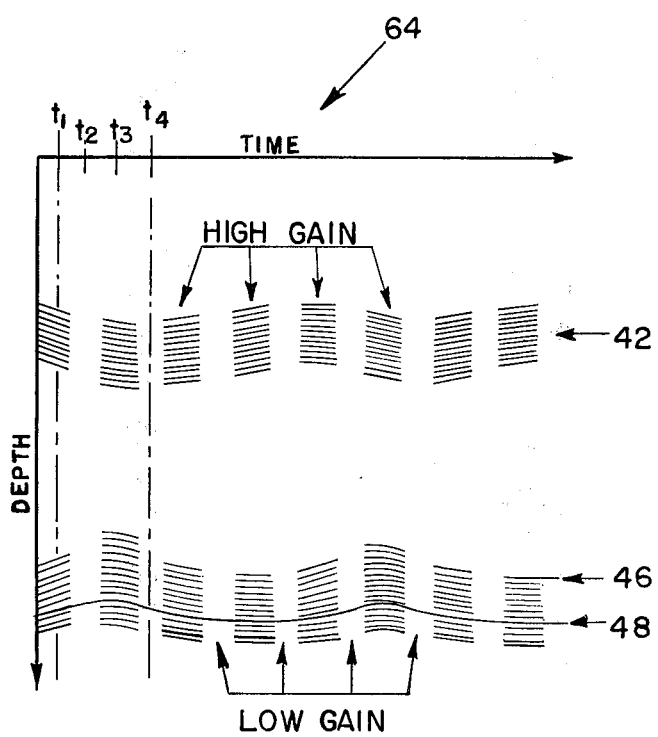
FIG. 2
FIG. 3

ULTRASONIC DIAGNOSTIC TECHNIQUE UTILIZING SWITCHED GAIN SIGNAL PROCESSING

BACKGROUND OF THE INVENTION

1. Field of the Invention

The present invention is related to ultrasonic diagnostic techniques and, more particularly, is directed towards an ultrasonic diagnostic technique for simplifying wall thickness measurement of cardiac structures.

2. Description of the Prior Art

Echocardiography constitutes a popular non-invasive technique in medical diagnostics which enables the visualization and measurement of cardiac structures. The technique comprises transmitting an ultrasonic pulse or signal towards the cardiac structure of interest and detecting the received echo signal reflected therefrom. A multi-surfaced cardiac structure will be responsible for a plurality of echo signals reflected back to the receiver. Detection of the depth from which the multiple signals originate at a particular instant of time provides data whereby the distance between two surfaces or components may be ascertained.

The pulse-echo ultrasonic technique described above has been particularly valuable in the quantification of ventricular septal and posterior wall thicknesses. See for example the Henry et al article "Asymmetric Septal Hypertrophy (Ash): Echo-Cardiographic Identification of the Pathogonomonic Anatomic Abnormality of IHSS" in the February, 1973, issue of *Circulation*, Volume 47 at page 677. The posterior wall of the left ventricle comprises an inwardly facing endocardial surface and an outer epicardial surface. The epicardial surface lies adjacent a wall of the lung, and the area is frequently referred to as the epicardial-lung interface.

In echocardiographic analysis of the left ventricular structure, it has been found that the signal reflected from the epicardial-lung interface is much stronger than that from the surrounding myocardium and lung. This is primarily due to the presence of air in the lung which causes a large change in the acoustic impedance of the ultrasonic signal at the epicardial-lung interface. The relatively large magnitude of the signal reflected from the epicardial-lung interface is often obliterated when the gain of the receiver is increased sufficiently to record the endocardial signal. In other words, as a result of the limited dynamic range and grey scale available in the typical displays or direct-writing recorders, effective simultaneous viewing of the epicardial and endocardial wall surfaces is difficult.

A swept gain feature is available on standard ultrasonic equipment and is utilized to normalize signal strength from various depths, thereby reducing the need for grey scale. However, the distance from the ultrasonic transducer to the myocardium changes both during the cardiac cycle and in accordance with the positioning of the transducer. Thus, the swept gain feature alone is not significantly helpful in clarifying the epicardial and endocardial surfaces.

Another attempted solution has been to first manually set the receiver to record several heartbeats at a low receiver gain to emphasize the epicardium, and then manually increase the gain and sensitivity to emphasize the endocardium surface. Data from the two sections of echocardiogram may then be combined to yield wall thickness. Although this approach has provided important diagnostic information, it requires stable transducer placement during both measurements which often is quite difficult to achieve. Further, it assumes that the heart dimensions do not change significantly with respiration, an assumption which can lead to erroneous readings. Further, this technique, being manual in nature, is quite tedious and time consuming.

The echo signal received in a typical diagnostic pulse-echo system has a useful dynamic range on the order of 100 dB. Approximately 50 dB of this range results from attenuation of echos from the deeper structures and therefore can be removed with swept gain. This leaves approximately 50 dB for display and recording. Most oscillographic recording systems, however, are unable to retain the 50 dB range. For example, a brightness modulated cathode ray tube is capable of only about 20 dB, while the popular direct-print paper retains only 15 dB (four grey levels). A variety of compression techniques may be utilized to reduce the signal's range, but resulting images are somewhat less than satisfactory.

OBJECTS AND SUMMARY OF THE INVENTION

It is therefore a primary object of the present invention to provide an improved ultrasonic diagnostic technique for processing pulse-echo signals which enable effective simultaneous viewing of the two posterior wall surfaces of the left ventricle.

A further object of the present invention is to provide an ultrasonic diagnostic technique utilized in connection with measuring the dimensions of the posterior wall of the left ventricle wherein the wide dynamic range of the echo signal may be matched to the high resolution of the recorder.

Another object of the present invention is to provide a technique for pulse-echo ultrasound wherein real time signal processing may be readily accomplished with standard pulse-echo equipment.

A still further object of the present invention is to provide an ultrasonic diagnostic technique which obviates all of the problems noted above with respect to prior art measurement techniques and thereby results in a greatly simplified time-saving clinical tool.

An additional object of the present invention is to provide a diagnostic technique utilizing pulse-echo ultrasonics which produces more accurate images of myocardial structure than heretofore possible.

A still further object of the present invention is to provide an ultrasonic diagnostic technique for visualization and measurement of cardiac structures whose accuracy is independent of stable transducer placement and the changing of heart dimensions with respiration.

The foregoing and other objects are attained in accordance with one aspect of the present invention through the provision of an ultrasonic diagnostic technique which utilizes switched gain signal processing. The gain switching technique effectively increases the dynamic range of the echocardiogram by alternately recording strong and weak echos in closely mixed areas. An oscillator, for example, may be utilized to electronically alternate the gain of the pulse-echo receiver between a high setting for detecting the endocardium echo and a lower setting for detecting the epicardium signal. Real time signal processing results in a readout which alternately displays the endocardial and epicardial surfaces. The gain switching technique improves the recording capacity of direct-print paper and is applicable to real time two-dimensional ultrasonic systems.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 2 illustrates a pair of graphs of the echo amplitude versus depth of the system of FIG. 1, also helpful in understanding the technique of the present invention; and FIG. 3 is an illustration of an echocardiogram with switched gain derived from the system of FIG. 1 in accordance with the principles and teachings of the preferred technique of the present invention.

DETAILED DESCRIPTION OF THE PRESENT INVENTION

Figure 1:
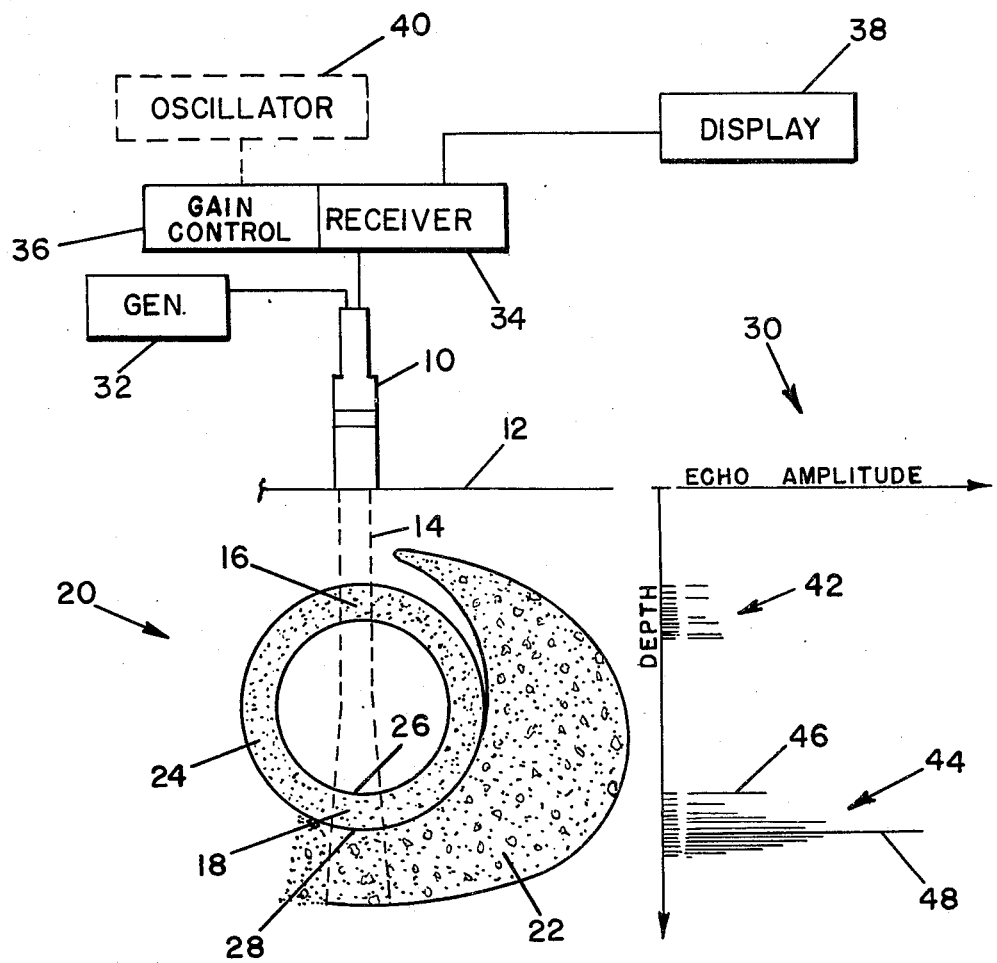
FIG. 1 is a diagrammatic representation illustrating a cardiac cross-section, an exemplary pulse-echo ultrasonic system, and the resultant echo signals received from the cardiac walls, all helpful in understanding the technique of the present invention.

Referring now to FIG. 1, there is illustrated a diagrammatic representation, indicated generally by the reference numeral 20, of the cross section of the cardiac structure of interest. The following description of the inventive diagnostic technique is described in connection with the visualization and measurement of left ventricular volume and wall thickness, and particularly with the posterior wall thickness measurement. It will be understood, however, by an ordinarily skilled technician, that the same principles may be applied to other cardiac structures where visualization and measurement by non-invasive diagnostic techniques are necessary.

The cardiac structure 20 includes the left ventricle 24 which is surrounded by lung 22 which extends around the left ventricle 24. The left ventricle 24 includes the forwardly positioned septum 16 and the posterior wall 18.

Posterier wall 18 is characterized by an inwardly facing endocardial surface 26 and an outer epicardial surface 28. Epicardial surface 28 is seen to lie adjacent a surface of lung 22, so as to form what is commonly referred to as the epicardial-lung interface, also indicated generally by reference numeral 28.

FIG. 1 also illustrates in block diagram form a common pulse-echo ultrasonic system utilized to measure the volume and wall thicknesses of left ventricle 24. The system utilizes an ultrasonic transducer 10 which is positioned adjacent the chest wall 12 of the patient under diagnostic care.

A generator 32 excites ultrasonic transducer 10 which, in turn, emits a sound beam 14 towards the cardiac structure of interest (in this example, the left ventricle). A receiver 34 is positioned to receive the reflected signals from the cardiac structure, which are then fed to a display unit 28, which may comprise, for example, a cathode ray tube, paper trace recorder, or the like.

Receiver 34 has associated therewith a gain control means 36, as is conventional. An oscillator 40 is shown in dotted outline and is connected to gain control means 36, oscillator 40 consisting of an apparatus for effectuating the inventive technique according to the present invention to be described in more detail hereinafter.

Reference numeral 30 of FIG. 1 designates a graph illustrating the amplitude of the various echo signals received from the ventricular walls of the cardiac structure 20. Graph 30 is drawn with a vertical axis corresponding to the depth of the signals below the chest wall 12, and a horizontal axis representing the amplitude of the received signals.

Illustrated at 42 are the echo signals received from ventricular septum 16, while at 44 are illustrated the group of signals received from the posterior wall 18. The group of echo signals 44 is seen to consist of a standard endocardial signal 46, and a much stronger typical epicardial signal 48. The strong echo signal 48 returning from the epicardial-lung interface results from the presence of air in the lung which causes a large change in the acoustic impedance at the epicardial-lung interface 28. Within posterior wall signal group 44, the ratio of the amplitudes of the epicardial signal 48 to the endocardial signal 46 is generally greater than 15 dB.

Referring now to FIG. 2, illustrated at 50 and 60 are two graphs of echo signals received from the cardiac structure 20 of FIG. 1. Graph 50 is exemplary of the echo signals received when the receiver 34 (FIG. 1) has a gain set at a relatively high level, while graph 60 is illustrative of the type of display obtainable with the receiver gain at a relatively low level.

Assuming that the display 38 (FIG. 1) of the apparatus comprises a common direct-print paper tracer, it can be seen by graphs 50 and 60 that the dynamic range of the paper, shown within the dashed lines 62, is insufficient to retain the endocardial signal 46 without obscuring the epicardial echo signal 48 in surrounding signals. This is most clearly seen in graph 50 which illustrates the signals received when the receiver gain is increased. The low intensity signals 42 and 46 from the septum and endocardium will be easily recorded, while the larger epicardial signal 48 cannot be distinguished from the surrounding echos as a result of the limited dynamic range of the paper.

However, as seen by graph 60, when the receiver gain is lowered, the septal and endocardial signals 42 and 46 will fall below the recording threshold and only the epicardial signal 48 will be recorded.

The present invention is therefore directed towards a technique of rapid gain switching between the high and low levels illustrated by graphs 50 and 60 that results in a well-defined posterior wall thickness.

Referring back to FIG. 1, in order to carry out the gain switching technique of the present invention, a common oscillator 40, which may, for example, be set to 200 Hertz, is connected to the gain control means 36 of receiver 34 to switch the gain thereof between two independently set levels. The lower gain will be selected to display the epicardium surface, while the higher gain may be adjusted to clearly display the endocardium.

A typical resultant echocardiogram 64 is illustrated in FIG. 3 and shows the time-dependent curve which result from the gain switching technique in accordance with the present invention. For example, at time $t_1$, the receiver 34 will be in its high gain state such that the septal and endocardial signals 42 and 46 will clearly appear. This also reoccurs a short while later at time $t_3$.

At alternate times $t_2$ and $t_4$, it is seen that the receiver, set to a relatively low gain and sensitivity, will illustrate only the epicardial signal 48, the septal and endocardial signals 42 and 46 falling below the threshold of the receiver and display 38. Although FIG. 3 illustrates relatively wide sections of each gain time, the frequency of oscillator 40 may be set sufficiently high to render loss of timing resolution negligible.

The frequency or switching rate of oscillator 40 employed will depend upon several factors, such as heart rate, recorder resolution, and the manner in which the human eye combines the section of an echocardiogram. According to experimentation, good results have been obtained by changing the gain after observing from two to ten data lines. That is to say, the gain is cycled through a high-low period at a rate of approximately 300 to 500 lines per cardiac cycle, depending on switching speed and heart rate. Extremely well defined posterior wall surfaces have been obtained with the technique of the present invention with gain switching at both 1 and 5 millisecond intervals.

The gain switching technique according to the present invention is highly useful since it effectively improves the recording capacity of direct-print paper. Further, the method is applicable to real time two-dimensional ultrasonic scanning. The gain switching diagnostic technique of the present invention matches the wide dynamic range of the echo signal to the high resolution of the recorder. Further, real time signal processing is readily accomplished with standard pulse-echo equipment. Manual intervention is eliminated, thereby saving a great deal of time and expediting the clinical examination. Finally, dependence upon steady transducer placement and minimal cardiac-respiratory movement are obviated.

Obviously, numerous modifications and variations of the present technique are possible in light of the above teachings. It is therefore to be understood that within the scope of the appended claims the invention may be practiced otherwise than as specifically described herein.

We claim as our invention:

1. A technique for measuring the wall thickness of a cardiac structure, which comprises the steps of: transmitting an ultrasonic signal towards the wall of the cardiac structure of interest; receiving ultrasonic echo signals reflected from said wall by means of a gain-variable receiver; switching the gain of said receiver repeatedly from a first value to a second value; and recording the output from said receiver.

2. The technique as set forth in claim 1, wherein said step of receiving ultrasonic echo signals reflected from said wall includes the step of simultaneously receiving signals reflected from the front and rear surfaces of said wall.

3. The technique as set forth in claim 2, wherein said step of repeatedly switching the gain of said receiver between said first and second values includes the step of selecting said first and second values so that the amplitude of said received signals from said front and rear surfaces of said wall respectively appear within said first and second values of gain of said receiver.

4. The technique as set forth in claim 3 wherein said step of repeatedly switching the gain of said receiver includes the step of connecting an oscillator to said receiver and setting the frequency of said oscillator to equal the rate at which the gain of said receiver is to be switched.

5. The technique as set forth in claim 1 wherein said cardiac structure comprises the left ventricle and wherein said wall comprises the posterior wall of said left ventricle.

6. The technique as set forth in claim 5 wherein said posterior wall includes an endocardial surface and an epicardial surface, said epicardial positioned adjacent the lung, and wherein said step of receiving ultrasonic echo signals reflected from the posterior wall includes the step of simultaneously receiving signals reflected from said endocardial and epicardial surfaces.

7. The technique as set forth in claim 6 wherein said step of repeatedly switching the gain of said receiver includes the step of selecting said first and second values so that the amplitude of said received signals from said endocardial and epicardial surfaces respectively appear within said first and second values of gain of said receiver.

8. The technique as set forth in claim 7 wherein said first value of gain is selected to be higher than said second value of gain.

* * * * *